United States Patent [19]

Roberts et al.

[11] Patent Number: 4,707,133

[45] Date of Patent: Nov. 17, 1987

[54] APPARATUS FOR PLASMA DIAGNOSTICS

[75] Inventors: Thomas G. Roberts, Huntsville; Raymond W. Conrad, Russellville; Thomas E. Honeycutt, Somerville, all of Ala.

[73] Assignee: The United States of America as represented by the Secretary of the Army, Washington, D.C.

[21] Appl. No.: 841,497

[22] Filed: Mar. 6, 1986

[51] Int. Cl.$^4$ ............................................. G01J 3/42
[52] U.S. Cl. .................................. 356/320; 250/565; 250/573; 356/328; 356/436
[58] Field of Search ............... 250/343, 344, 345, 573, 250/565; 356/319, 320, 326, 328, 329, 330, 331, 332, 333, 334, 407, 435, 436, 437, 438, 439

[56] References Cited

U.S. PATENT DOCUMENTS 3,510,665  5/1970  Goolsby ............................. 250/565
4,426,640  1/1984  Beeconsall et al. ................. 340/632
4,516,858  5/1985  Gelbwachs ......................... 356/437

OTHER PUBLICATIONS

Marrodineumu et al., Applied Optics vol. 7, No. 7 pp. 1281-1285.
R. M. Measures, "Spectral Line Interferometry: A Proposed Means . . . Population,"Applied Optics, vol. 9, No. 3, Mar. 1970, pp. 737-741.
H. Odenthal et al., "Determination of Temperature . . . Atomic Resonances," IEEE Transactions on Plasma Science, vol. PS-8, No. 4, Dec. 1980, pp. 431-436.
R. H. Huddlestone & S. L. Leonard, Editors, "Plasma Diagnostic Techniques," Academic Press, 1965 (contents).

Primary Examiner—F. L. Evans
Assistant Examiner—Frederick N. Samuels
Attorney, Agent, or Firm—John C. Garvin, Jr.; Freddie M. Bush

[57] ABSTRACT

A system for measuring the density of certain ions or neutrals within a plasma without probe intervention. When cylindrical symmetry is present, the system also provides measurement of spatial distribution of excited ionic states within the plasma. The system allows spatial distribution of contaminant ions in magnetic confinement thermonuclear fusion devices to be monitored. These functions are accomplished by directing two laser beams through a region containing a plasma. The laser means are at respective wavelengths chosen to be in and closely adjacent to a spectral region near the electronic transition frequency of the ionic species of interest in the plasma. The intensities of the two wavelengths are then measured and compared to obtain the desired data and characterization.

6 Claims, 2 Drawing Figures

APPARATUS FOR PLASMA DIAGNOSTICS

DEDICATORY CLAUSE

The invention described herein may be manufactured, used, and licensed by or for the Government for governmental purposes without the payment to us of any royalties thereon.

BACKGROUND OF THE INVENTION

Interest in high energy plasmas for applications in propulsion, thermonuclear fusion, space defense, short wavelength lasers, and materials development has stimulated considerable research into their production, confinement, acceleration, and propagation. New efforts in space defense have included plasmoids and collective acceleration of ions. Plasmoids have been launched using button guns, coaxial theta pinches, coaxial rail guns, and Z-pinch guns. Collective acceleration of ions by relativistic electron beams and self Z-pinch generators has been demonstrated. Coaxial theta pinch produces vortex rings having electron densities in the range of $10^{15}$ to $10^{16}/cm^3$ and ion temperatures from 10 to 1000 ev (electron volts), button guns produce plasmoids with lower electron temperatures and propagation velocities in the range of $10^6$ cm/sec, while collective ion accelerators produce ions with velocities as high as 0.1 c (c is the velocity of light) which corresponds to energies of 4.7 MeV per atomic mass unit. Additionally, x-ray lasing from laser produced plasmas has only recently been obtained.

To evaluate and characterize these plasmas, diagnostic techniques have been developed for more than 40 years. Magnetic probes, double probes, microwave interferometers, optical line broadening techniques, neutron emission and laser scattering techniques have been used. Faraday cups, Thomas parabolas, secondary-ion mass spectrometry, and other high energy dosimeters are used with relativistic electron beam and ion acceleration experiments. These various diagnostic techniques provide average properties of the plasmas. Even the ion temperatures and densities inferred from line broadening measurements and the electron densities inferred from laser scattering and microwave interferometry do not give spatially resolved information. However, many of these plasmas are produced with cylindrical symmetry and with energies such that an appropriately developed nonintrusive diagnostic method can replace the probe measurement techniques currently used. Also in many cases, as is the case in magnetic confinement thermonuclear fusion devices, probes cannot be used because of their introduction of contaminating ions into a system.

Prior art references disclosing further background to the invention and pertinent to the background summarized hereinabove are listed below as follows:

1. E. G. Harris, R. B. Theus, and W. H. Bostick, "Experimental Investigations of the Motion of Plasma Projected from a Button Source Across Magnetic Fields," Physics Review 105, p. 46 (1959).
2. R. L. Small, E. A. Valsamakis, and W. H. Bostick, "Probe Measurements of Plasma Rings Injected into an Axial Guide Field," AIAA Journal 5, p. 853 (1967).
3. D. R. Wells, P. Ziajka, and J. Tunstall, "Ion Temperature Infrared from Neutron Yield Measurements in the TRISOPS IIX Plasma Vortex Structure Generator," Journal of Plasma Physics 34, p. 39 (1984).
4. Y. Ito, H. Nishida, S. Gato, and T. Ishimura, "A Pulsed Neutral Particle Source for Active Plasma Diagnostics," Japan Journal of Applied Physics 21, p. 912 (1982).
5. W. W. Destler, L. E. Floyd, and M. Reiser, "Collective Acceleration of Heavy Ions," Physics Review Letters 44, p. 70 (1980).
6. R. J. Adler and J. A. Nation, "Collective Acceleration of Metallic Ions," Applied Physics Letters 36, p. 810 (1980).
7. W. W. Destler, and J. T. Gemer, "Charge-state Measurement of Collectively Accelerated Heavy Ions," Journal of Applied Physics 54, p. 636 (1983).
8. T. G. Roberts et al, "Simple Solid-Electrolyte Gamma-Ray and Relativistic-Charged Particle Dosimeters," U.S. Pat. No. 3,585,389.
9. T. G. Roberts, "Radiation Energy Detector and Analyzer," U.S. Pat. No. 4,289,966.
10. R. M. Measures, "Spectral Line Interferometry: A Proposed Means of Selectively Measuring the Change in Density of a Specific Atomic Population," Applied Optics 9, p. 737 (1970).
11. H. Odenthal and J. Hlenbush, "Determination of Temperature, Velocity Distribution, and Population Densities of Neutral Helium by Means of Laser Light Tuned on Atomic Resonances," IEEE Transactions Plasma Science PS-8, p. 431 (1980).
12. C. M. West, *Holographic Interferometry*, John Wiley and Sons, New York (1979).
13. H. R. Griem, *Spectral Line Broadening by Plasmas*, Academic Press, New York (1984).
14. "Plasma-Diagnostic Techniques" edited by R. Huddlestone and S. Leonard, Academic Press (1965).

SUMMARY OF THE INVENTION

The plasma diagnostics apparatus provides a means for measuring the density of certain ions or neutrals within the plasma without probe intervention. In the special case where cylindrical symmetry exists, it also provides measurement of the spatial distribution of excited ionic states within the plasma. The apparatus also allows monitoring of the spatial distribution of contaminant ions in magnetic confinement thermonuclear fusion devices. These functions are accomplished by directing two laser beams through a plasma at respective wavelengths chosen to be in and adjacent to a spectral region near the electronic transition frequency of the ionic species of interest. The intensities of the two wavelengths are then measured and compared to obtain the desired data and characterization.

DESCRIPTION OF THE PREFERRED EMBODIMENT

Figure 1:
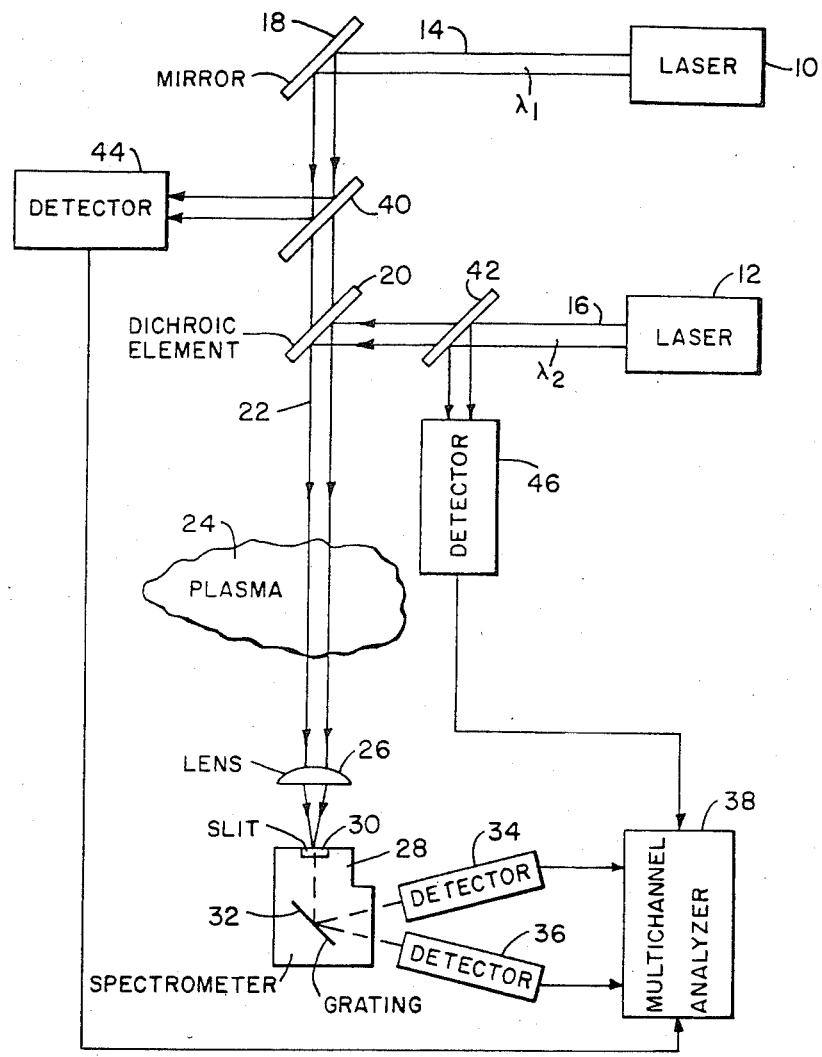
FIG. 1 is a single line schematic representation of a preferred embodiment of the system for providing the plasma diagnostics.

Referring to FIG. 1 of the drawings, the diagnostic apparatus comprises two lasers, optical means for joining and collimating the two laser beams from the lasers, a filter or spectrographic slit, a region for beam forming, a grating to separate the two laser beams, detectors for each wavelength, and signal processing circuitry for extracting and recording the difference in beam intensity. First and second tunable lasers 10 and 12 are commonly pumped dye lasers or simultaneously triggered lasers that provide output beams along respective paths 14 and 16. Optical means such as a single diffraction grating (not shown) or the combination of a mirror 18 and dichroic element 20 are introduced into the optical paths 14 and 16 for joining and collimating a primary portion of each beam into output beam path 22, wherein mirror 18 is in beam path 14 and dichroic 20 is in beam path 16 and also receives the beam portion reflected from mirror 18. The composite beam path 22 is directed through a region established for plasma development. Thus, when a plasma 24 is formed in the region the composite beams pass through the plasma to a lens 26 and are directed to receiving circuitry. Generally, the receiving circuitry may be a spectrometer 28 having a spectrographic slit 30 therein for directing the multiple beams to a grating 32. The grating separates the two beams. Detectors 34 and 36 are located in the paths of the separated beams for detecting respective beam intensities. Output electrical signals from the detectors are coupled to indicating circuitry for subsequent processing and/or display. Typical of such indicating circuitry are a recorder, an oscilloscope, or the multichannel analyzer 38 shown in FIG. 1. Additionally, beamsplitters 40 and 42 are placed respectively in the reflected beampath 14 and beampath 16 for sampling a portion of the beam intensity of each beam. The sampled portion of beam intensity from beamsplitter 40 is coupled to a detector 44, and the intensity sampled by beamsplitter 42 is coupled to detector 46. The electrical signal outputs of detectors 44 and 46 are coupled to the indicating circuitry for selective combination with the outputs of the other detectors. Detectors 44 and 46 measure the relative intensities of their respective beams. Thus, assuming the output of detector 34 to be detected intensity of energy from beam path 14 that has passed through the plasma, the outputs of detectors 34 and 44 are combined at indicating circuitry 38 to provide relative attenuation. Similarly, the output from detectors 36 and 46 are combined at indicating circuitry 38 to provide relative attenuation for the intensity of energy in beam path 16. These two resultant intensity signals are then combined and the difference output obtained from the indicating circuitry or analyzer 38.

The two wavelengths of the lasers are selected so that one wavelength (laser 10) is in a spectral region near but not coincident with the electronic transition frequency of the ionic species in plasma 24 that is to be measured. The development of tunable dye lasers now makes it possible to tune the second laser 12 to coincide with the electronic transition frequency of interest. Thus, each of the above lasers are tunable so that different ionic species may be sampled. The only exception to this case occurs when a magnetic confinement thermonuclear device is being monitored for one particular contaminate ion (such as, for example, one of the materials of which a containment wall is made) near a diverter that is designed to remove the contaminate ions. The filter or slit is used to keep light from the plasma in spectral regions other than those near the laser frequencies from reaching the detectors. The light after passing through the filter or slit 30 is then separated by the grating 32 or by a dichroic beam splitter. After the laser beams have been separated each is detected and the concentration of the ions of interest is determined from the difference in the respective attenuations of these signals. The two detectors might be replaced by one using moveable optical elements to alternately expose the detector to one beam and then the other, but this configuration is not preferred.

In operation, when there are little or no ions at or near resonance the two laser beams interact primarily with the electrons through the known process of inverse bremsstrahlung. Since the two wavelengths are fairly close together the attenuation for both is very nearly the same. However, when ions are present with an electronic transition frequency which coincides with one of the laser frequencies, the contribution of the resonating specie can be very large compared to the electron contribution. In this case, the attenuation due to the electron distribution as determined by the off-resonance laser line can be subtracted from the total attenuation of the on-resonance line to give the contribution of the ions. As an example, consider the case where singly-ionized argon is a contaminate in a hydrogen plasma. It is established technology that the concentration of argon ions in the particular 3p4s 4P state are in resonance with radiation at 0.4875 $\mu$m wavelength. Tuning one of the lasers to this wavelength and, for example, the other laser to 0.4750 $\mu$m, then densities as low as one part per thousand can be detected. One part per thousand corresponds to densities as low as $10^{12}/cm^3$ in a typical plasma of 4 inch diameter with a density of $10^{15}/cm^3$ at a temperature of 10 eV.

Although not shown, a third laser can be added to the system to simultaneously measure the density profile of another electronic energy level of the argon ion and these two results can be used to infer a temperature profile for the plasma. This temperature extraction is well known to those skilled in the art. Also, since many of the plasmas being investigated possess cylindrical symmetry it will also be necesary to Abel invert the data to obtain the density profiles as a function of the radius of the plasma, but again these techniques are well known in the art.

Operation of the system of FIG. 1 is limited to or controlled by the bandpass and band rejection characteristics of dichroic element 20. Therefore, if the wavelengths from lasers 10 and 12 are so close together (for example less than 25 Angstroms of separation) that a dichroic element is difficult to use or that a narrow bandpass filter cannot be used as the dichroic, then the system of FIG. 2 is appropriate.

Figure 2:
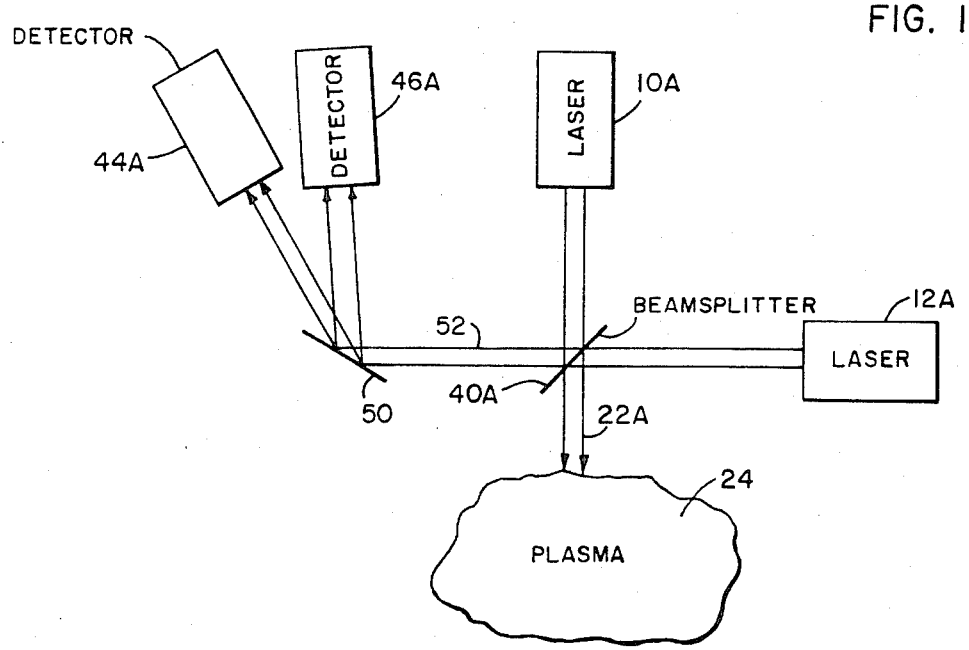
FIG. 2 is a partial schematic representation of an alternative embodiment.

FIG. 2 is a partial schematic showing only that portion of the FIG. 1 circuitry that is changed by removing the dichroic element. Thus, in FIG. 2, elements 10A, 12A, 40A, 44A, and 46A are the same elements as set forth in FIG. 1 by the same numbers. Elements 18, 20 and 42 are removed, and a new element, grating 50, is added. The two lasers 10A and 12A have outputs directed to beamsplitter 40A. Output path 22A from the beamsplitter includes a portion of the beam from laser 10A that passes through element 40A and a portion of the beam from laser 12A that is reflected from element 40A. This composite beam is directed through the plasma and processed as noted in FIG. 1. The reflected portion of the beam from laser 10A and the passed portion of the beam from laser 12A is directed along path 52 to grating 50. The respective laser wavelengths are then divided by grating 50 into two paths, directing the beam portion originating from laser 10A to detector 44A, for example, and the beam portion from laser 12A to detector 46A. Otherwise, operation of the systems of FIGS. 1 and 2 is identical.

Although a particular embodiment and form of the invention has been described, it will be obvious to those skilled in the art that modifications may be made without departing from the scope and spirit of the foregoing disclosure.

We claim:

1. Diagnostic apparatus comprising: first and second tunable lasers for providing first and second output beams, optical means adjacent said lasers for bringing together and collimating the two laser beams and directing the beams along a path through a space, receiving means in the path of said two laser beams for selecting the two laser beams from extraneous radiation and separating the composite beams into first and second beampaths, said receiving means being on the opposite side of the space from said optical means, first and second detectors in respective beampaths, each detector being for receiving the respective laser beam and providing an electrical output indicative of the beam intensity, signal processing means coupled to receive said electrical outputs for combination to provide an indication of relative changes in intensity between the first and second beams after their passage through said space, and a plasma in said space and wherein said first and second lasers are tuned to respective adjacent wavelengths so that the wavelength from said first laser is tuned to a spectral region near a predetermined first electronic transition frequency present in said plasma, and second laser is tuned to substantially coincide with said electronic transition frequency present in said plasma, thereby allowing different ionic species of the plasma to be sampled.

2. Diagnostic apparatus as set forth in claim 1 wherein said optical means comprises a mirror and a dichroic element, said mirror directing the first laser beam to said dichroic element, said diohroic element passing said first laser beam and receiving and reflecting said second laser beam along the path with said first beam into said space.

3. Diagnostic apparatus as set forth in claim 2 wherein said receiving means comprises a spectrographic slit for receiving and filtering said laser beams for extraneous radiation wavelengths and a diffraction grating for separating the beams into the first and second beampaths, and wherein said signal processing means is a multichannel analyzer.

4. Diagnostic apparatus as set forth in claim 3 and further comprising third and fourth detectors and first and second beamsplitters, said first beam splitter being disposed between said first laser and said dichroic element for removing a sample of the first beam intensity and coupling said sample to said third detector, said third detector having an electrical output indicative of said first beam intensity and said output being coupled to said analyzer, said second beam splitter lying between the second laser and the dichroic element for diverting a sample of the second beam intensity to said fourth detector, said fourth detector coupling an electrical output indicative of the beam intensity to said analyzer, and said analyzer subtractively combining the inputs from the first and third detectors and the inputs from the second and fourth detectors to provide signals indicative of beam changes in the respective first and second beam intensities, these signals indicative of changes in beam intensity are then combined differentially and recorded by the analyzer for providing an output signal indicative of ionic density, spatial distribution of excited ionic states within a plasma.

5. Diagnostic apparatus as set forth in claim 1 wherein said optical means is a beamsplitter for passing a portion of the first laser beam therethrough and reflecting a portion of said second laser beam therefrom along a first composite beam path, said composite beam path being the path through said space; said beamsplitter further passing a portion of the second laser beam therethrough and reflecting a portion of said first laser beam therefrom along a second composite beam path; and further comprising third and fourth detectors and a grating, said grating receiving said beam portions on said second composite beam path, separating the beam portions into separate paths and directing them to respective ones of said third and fourth detectors, said third detector having an electrical output indicative of the intensity of said first laser beam and said output being coupled to said signal processing means, said fourth detector having an electrical output indicative of the intensity of the second laser beam, said output being coupled to said signal processing means, said signal processing means subtractively combining the inputs from the first and third detectors and the inputs from the second and fourth detectors to provide signals indicative of beam changes in the respective first and second beam intensities and then further combining these signals, indicative of changes in beam intensity, differentially for providing an output signal indicative of ionic density, spatial distribution of excited ionic states within a plasma.

6. Diagnostic apparatus as set forth in claim 5 wherein said receiving means comprises a spectrographic slit for receiving and filtering said laser beams for extraneous radiation wavelengths and a diffraction grating for separating the beams into the first and second beampaths, and wherein said signal processing means is a multichannel analyzer.

* * * * *